United States Patent
Willard

(10) Patent No.: US 6,669,886 B1
(45) Date of Patent: Dec. 30, 2003

(54) REINFORCED CATHETER AND METHOD OF MANUFACTURE

(75) Inventor: Martin Willard, Burnsville, MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 468 days.

(21) Appl. No.: 09/631,800

(22) Filed: Aug. 3, 2000

(51) Int. Cl.[7] ............................................... B29C 47/06
(52) U.S. Cl. ........................... 264/171.14; 264/171.16; 264/171.26; 264/210.2; 604/524
(58) Field of Search .................. 604/524; 264/171.14, 264/127, 171.16, 171.2, 171.26, 171.29, 173.13, 209.1, 210.2, 248, 249, 296, 323, 331.34

(56) References Cited

U.S. PATENT DOCUMENTS

| | | |
|---|---|---|
| 1,481,078 A | 1/1924 | Albertson |
| 3,731,671 A | 5/1973 | Magoeh ................. 128/2.05 R |
| 3,879,516 A | 4/1975 | Wolvek |
| 4,020,829 A | 5/1977 | Willson et al. ............ 128/2 M |
| 4,044,765 A | 8/1977 | Kline ...................... 128/214.4 |
| 4,052,989 A | 10/1977 | Kline .................... 128/349 R |
| 4,430,083 A | 2/1984 | Ganz et al. .................. 604/283 |
| 4,495,134 A | 1/1985 | Ouchi et al. ................ 264/516 |
| 4,516,972 A | 5/1985 | Samson ...................... 604/282 |
| 4,737,153 A | 4/1988 | Shimamura et al. ........ 604/282 |
| 4,842,590 A | 6/1989 | Tanabe et al. ............... 604/282 |
| 4,907,624 A | 3/1990 | Jonasson .................... 138/125 |
| 4,917,666 A | 4/1990 | Solar et al. .................. 604/95 |
| 5,019,057 A | 5/1991 | Truckai |
| 5,069,674 A | 12/1991 | Fearnot et al. .............. 604/282 |
| 5,125,895 A | 6/1992 | Buchbinder et al. .......... 604/95 |
| 5,334,169 A | 8/1994 | Brown et al. ................ 604/282 |
| 5,419,373 A * | 5/1995 | May ........................... 138/108 |
| 5,591,142 A | 1/1997 | Van Erp |
| 5,778,941 A * | 7/1998 | Inada ......................... 138/134 |
| 5,827,242 A | 10/1998 | Follmer et al. |
| 6,053,903 A | 4/2000 | Samson |
| 6,305,428 B1 * | 10/2001 | Nakamura et al. .......... 138/126 |

FOREIGN PATENT DOCUMENTS

| | | |
|---|---|---|
| WO | WO 98/24502 | 6/1998 |
| WO | WO 99/64097 | 12/1999 |

* cited by examiner

*Primary Examiner*—Mark Eashoo
(74) *Attorney, Agent, or Firm*—Crompton, Seager & Tufte, LLC

(57) ABSTRACT

A catheter shaft is disclosed that may reduce the thickness of the inner layer and/or may allow the reinforcing layer to share the same space as the inner lubricious layer. In one illustrative embodiment, the inner lubricious layer is removed altogether, and an inner tubular braid member defines the inner lumen of the catheter shaft. In another illustrative embodiment, the inner lubricious layer and the reinforcing layer are effectively combined to form a reinforcing member. To combine the inner lubricious layer and the reinforcing layer, the wires used to form the reinforcing braid or coil are first coated with a lubricious polymer such as PTFE or PFA. When these strands are wound to form the tubular reinforcing member, the inner surface of the reinforcing member includes a lubricious surface. Various methods are also disclosed for providing a smooth inner surface for the catheter shaft.

24 Claims, 3 Drawing Sheets

REINFORCED CATHETER AND METHOD OF MANUFACTURE

TECHNICAL FIELD

The present invention generally relates to the field of intravascular medical devices, and more specifically to the field of catheters such as guide catheters used for the placement of medical devices and diagnostic catheters used to inject radiopaque fluids within the body for treatment and diagnosis of vascular diseases. In particular, the present invention relates to an improved reinforced guide or diagnostic catheter and methods of manufacture.

BACKGROUND OF THE INVENTION

Several types of catheters are utilized for intravascular treatment. Examples of intravascular catheters include guide catheters, angioplasty catheters, stent delivery devices, angiography catheters, neuro catheters, and the like.

Guide catheters are commonly used during coronary angioplasty procedures to aid in delivering a balloon catheter or other interventional medical devices to a treatment site in a coronary vessel. In a coronary angioplasty procedure, a guide catheter is introduced into a peripheral artery and advanced over a guidewire through the aorta until the distal end of the guide catheter is engaged with the appropriate coronary ostium. Next, a balloon dilatation catheter is introduced over a guidewire and through the guide catheter. The guidewire is advanced past the distal end of the guide catheter within the lumen of the diseased vessel and manipulated across the region of the stenosis. The balloon dilatation catheter is then advanced past the distal end of the guide catheter, over the guidewire, until the balloon is positioned across the stenotic lesion. After the balloon is inflated to dilate the blood vessel in the region of the stenotic lesion, the guidewire, balloon dilatation catheter and guide catheter are withdrawn.

Guide catheters typically have preformed bends formed along their distal portion to facilitate placement of the distal end of the guide catheter into the ostium of a particular coronary artery of a patient. In order to function efficiently, guide catheters generally require a relatively stiff main body portion and soft distal tip. The stiff main body portion gives the guide catheter sufficient "pushability" and "torqueability" to allow the guide catheter to be inserted, moved and rotated in the vasculature to position the distal end of the catheter at the desired site adjacent to a particular coronary artery. However, the distal portion should have sufficient flexibility so that it can track over a guidewire and be maneuvered through a tortuous path to the treatment site. In addition, a soft distal tip at the very distal end of the catheter should be used to minimize the risk of causing trauma to a blood vessel while the guide catheter is being moved through the vasculature to the proper position.

Angiography catheters can be used in evaluating the progress of coronary artery disease in patients. Angiography procedures are used to view the patency of selected blood vessels. In carrying out this procedure, a diagnostic catheter having a desired distal end curvature configuration may be advanced over a guidewire through the vascular system of the patient until the distal end of the catheter is steered into the particular coronary artery to be examined.

For most intravascular catheters, it is desirable to have both a small outer diameter and a large inner lumen. Having a small outer diameter allows the catheter to be maneuvered more easily once inserted into the body, and may allow the catheter to reach more distal sites. Having a large inner lumen allows larger medical appliances to be inserted through the catheter and/or allows a higher volume of fluids to be injected through the inner lumen. To minimize the outer diameter of the catheter and maximize the inner diameter of the inner lumen, a relatively thin catheter wall is needed.

Thin-walled catheters formed strictly from polymers such as polyether block amide often do not have sufficient strength to be useful in many medical procedures. The pushability, torqueability, kinkability and other characteristics are often not acceptable. One way to increase the strength of such a thin-walled catheter is to provide a reinforcing braid or coil in the catheter wall. One such catheter is shown in U.S. Pat. No. 4,516,972 to Samson. Samson discloses an intravascular catheter that has an inner lubricious layer (e.g., PTFE), an intermediate reinforcing layer (braid), and an outer layer. The inner lubricious layer reduces the friction of the wall of the inner lumen, which is particularly useful when dilatation catheters or other medical devices are passed through the inner lumen. The braided reinforcing layer is braided over the lubricious layer, and the outer layer is extruded over the reinforcing layer.

While Samson improves the strength of the catheter wall, the ability to minimize the thickness of the catheter wall is limited. For example, the minimum thickness of the inner lubricous layer of Samson typically must be sufficiently thick to ensure that the lubricious layer remains structurally intact during subsequent processing steps, such as when the reinforcing layer is braided thereover. In addition, the braided reinforcing layer does not penetrate the outer surface of the inner lubricious layer. Instead, the braided reinforcing layer overlays the outer surface of the lubricious layer. As such, the braided reinforcing layer does not share the same space as the inner lubricious layer, thereby adding to the overall thickness of the catheter wall. Finally, because three separate layers must be assembled to form the catheter, the manufacturing costs may be relatively high.

SUMMARY OF THE INVENTION

The present invention provides a reinforced catheter shaft that may have a reduced wall thickness and/or lower manufacturing cost than the prior art. This is preferably achieved by eliminating or reducing the thickness of the inner lubricious layer and/or allowing the reinforcing layer to share the same space as the inner lubricious layer. In one illustrative embodiment, the inner lubricious layer is removed altogether, and an inner tubular formed braid member defines the inner lumen of the catheter shaft. In another illustrative embodiment, the inner lubricious layer and the reinforcing layer are effectively combined to form a reinforcing member. This is accomplished by, for example, coating the wires used to form the reinforcing member with a lubricious polymer such as polytetrafluoroethylene (PTFE) or perfluoroalkoxy (PFA) to first form coated wire. When these coated wires are wound or braided on a mandrel to form the tubular reinforcing member, the inner surface of the reinforcing member includes the lubricious polymer exposed to the inner lumen and forming the lumen wall.

To provide a smooth inner surface on the lumen wall, the braided or wound reinforcing member may first be disposed on a mandrel that has a relatively smooth outer surface. Heat and/or pressure may then be used to cause the lubricious polymer that coats the core wires of the reinforcing member to conform to the outer surface of the mandrel.

If a non-thermoplastic polymer such as PTFE is used to coat the core wires, significant heat and pressure may be required to induce the non-thermoplastic polymer to conform to the outer surface of the mandrel. In such a case, the mandrel may be metallic, and more specifically, may be copper or copper coated with silver. If a thermoplastic polymer such as a perfluoroalkoxy polymer (PFA or MFA) is used to coat the core wires of the reinforcing member, less heat may be required to induce the thermoplastic polymer to flow and conform to the smooth outer surface of the mandrel. Accordingly, the mandrel may be made from a polymer, such as acetyl polymer. In this latter case, the cost of the mandrel may be significantly reduced relative to a copper or silver coated copper mandrel. In either case, an outer layer is preferably extruded over the reinforcing member to provide additional support to the catheter shaft and to provide a smooth outer surface.

BRIEF DESCRIPTION OF THE DRAWINGS

The invention will be further described with reference to the accompanying drawings where like numbers refer to like parts in several views and wherein.

DETAILED DESCRIPTION OF THE PREFERRED EMBODIMENTS

Figure 1:
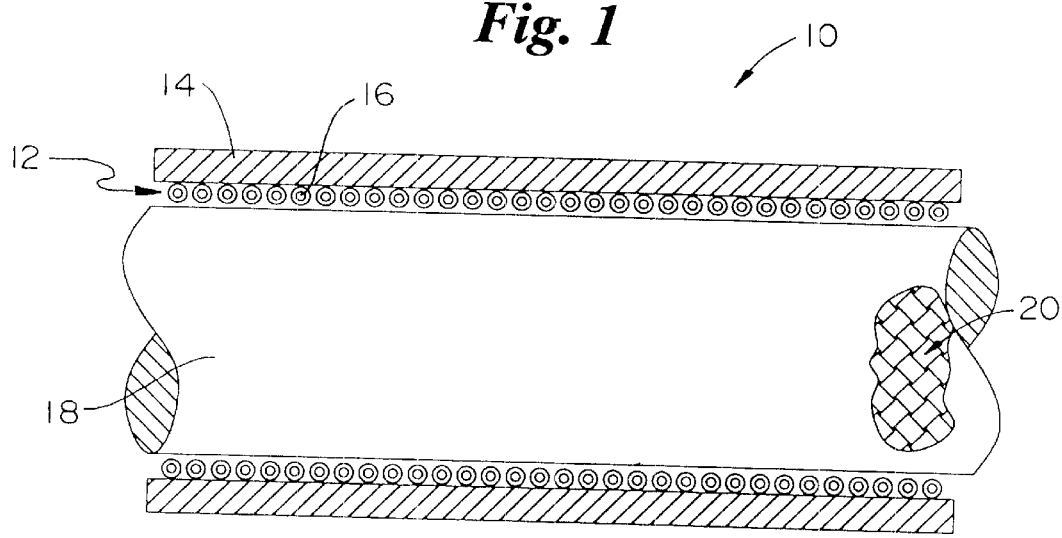
FIG. 1 is a partial cross-sectional side view of an illustrative catheter shaft in accordance with the present invention.

FIG. 1 is a partial cross-sectional side view of an illustrative catheter shaft in accordance with the present invention. The catheter shaft is generally shown at 10, and includes an inner tubular reinforcing member 12 surrounded by an outer layer 14. The inner tubular reinforcing member 12 is preferably formed from one or more strands 16 that are wound or braided around a mandrel 18. The outer diameter of the mandrel 18 is sized to correspond to the desired inner diameter of the inner lumen of the catheter shaft 10. When the mandrel 18 is removed, the inner tubular reinforcing member 12 defines the inner lumen of the catheter shaft 10.

The strands 16 of the reinforcing member can be wound in any pattern including a coil or braid pattern. A braid pattern is shown in the partial cut-away region 20 of FIG. 1. When a braid pattern is provided, it is contemplated that the braid angle may be adjusted to provide the desired flexibility to the shaft 10, and may be varied along the length of the shaft 10. In one embodiment, each strand of the braid or coil is a wire, such as a stainless steel wire.

Once the inner tubular reinforcing member 12 is formed around the mandrel 18, outer layer 14 is provided. The outer layer 14 is preferably extruded over the outer surface of the inner tubular reinforcing member 12. In some embodiments, it may be desirable to prevent the outer layer 14 from flowing through the inner tubular reinforcing member 12, and to the mandrel 18. In these embodiments, a tight braid pattern may be used when forming the inner tubular reinforcing member 12. Once the outer layer 14 is provided, the mandrel 18 is removed, leaving a hollow catheter shaft 10. The outer layer 14 is preferably formed from polyester, polyether block amide, nylon, or some other thermoplastic polymer.

Figure 2:
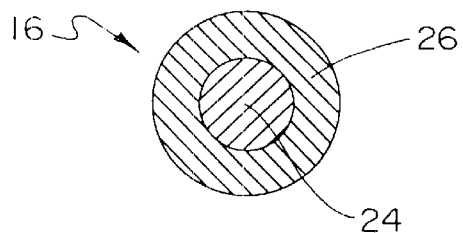
FIG. 2 is a cross-sectional side view of an illustrative strand used in forming the reinforcing member of FIG. 1.

When additional lubricity is desired in the inner lumen of the catheter shaft 10, each strand of the braid or coil may be a composite of an inner core wire 24 that is coated with a polymer 26, such as shown in FIG. 2. The polymer 26 may be used to increase the lubricity of the inner surface of the inner lumen of the catheter shaft 10. As such, the polymer 26 may be a lubricious polymer such as polytetrafluoroethylene (PTFE) or perfluoroalkoxy (PFA or MFA). PFA and MFA, both perfluoroalkoxy polymers, are available from Ausimont, S.P.A. Utilizing the above-described method of manufacture, when the mandrel 18 is removed, the wound or braided polymer coated core wire 24 defines the inner lumen of the catheter shaft 10. The polymer coating, as braided or wound, is exposed and will contact a device passed through the lumen, thus providing a lubricious surface which has a surface contour defined by the braid or coil pattern. Alternatively, or in addition to, the polymer 26 may be used to provide a smooth inner surface to the inner lumen by modifying the above method, as further described below.

Figure 3:
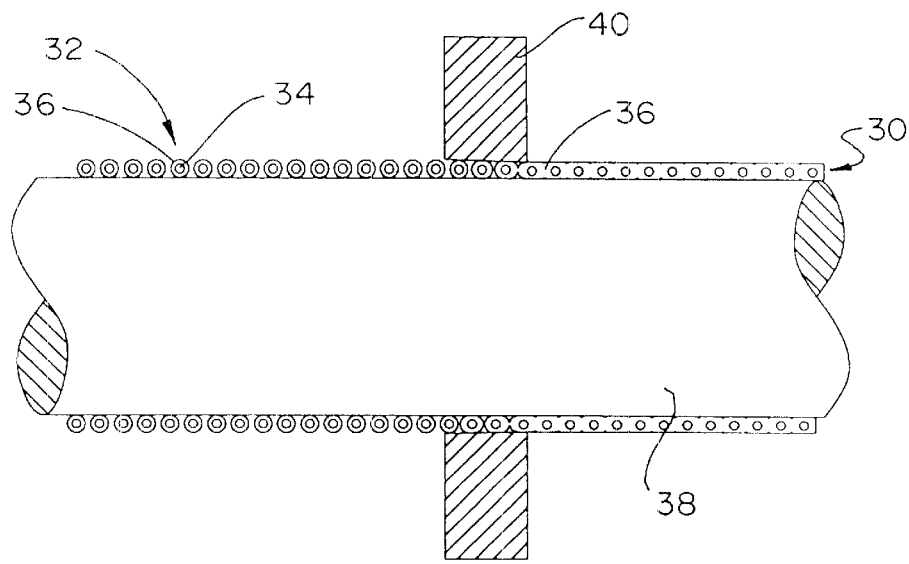
FIG. 3 is a partial cross-sectional side view of a reinforcing member passing through a heated die.

FIG. 3 is a partial cross-sectional side view of a reinforcing member 30 that is being passed through a heated die 40. The reinforcing member 30 includes one or more strands 32 wound in a coil or braid pattern, as described above. Each strand 32 is shown having an inner core 34 made from stainless steel or the like with a thermoplastic polymer coating 36. The thermoplastic polymer coating 36 is preferably formed from a lubricious thermoplastic polymer such as a perfluoroalkoxy polymer. For applications where lubricity is not necessary, as in some diagnostic applications, any suitable thermoplastic polymer could be utilized.

To provide a relatively smooth inner surface to the catheter shaft, the reinforcing member 30 is wound or braided on a mandrel 38, which has a relatively smooth outer surface. The reinforcing member 30, along with the mandrel 38, is then passed through heated die 40. The heated die 40 causes the thermoplastic polymer 36 to conform to the outer surface of the mandrel 38 and the inner surface of the heated die 40. The thermoplastic polymer 36 also tends to fill the interstitial sites between the windings of the braid or coil pattern. Accordingly, a thin-walled inner liner that is impregnated with the core wire windings is provided along the length of the catheter shaft.

The heat required to flow many thermoplastic polymers can be relatively low. As such, the mandrel 38 need only be made from a material that has a flow temperature that is higher than the flow temperature of the thermoplastic polymer 36 used to coat the core wires 34 of each strand of the reinforcing member. When the thermoplastic polymer of each strand is a perfluoroalkoxy polymer, for example, the mandrel may be made from an acetyl polymer. By using a polymer mandrel, rather than a copper or silver coated copper mandrel, the cost of the mandrel may be significantly reduced. In any event, an outer layer (not shown) is preferably extruded over the reinforcement member 30.

Figure 4:
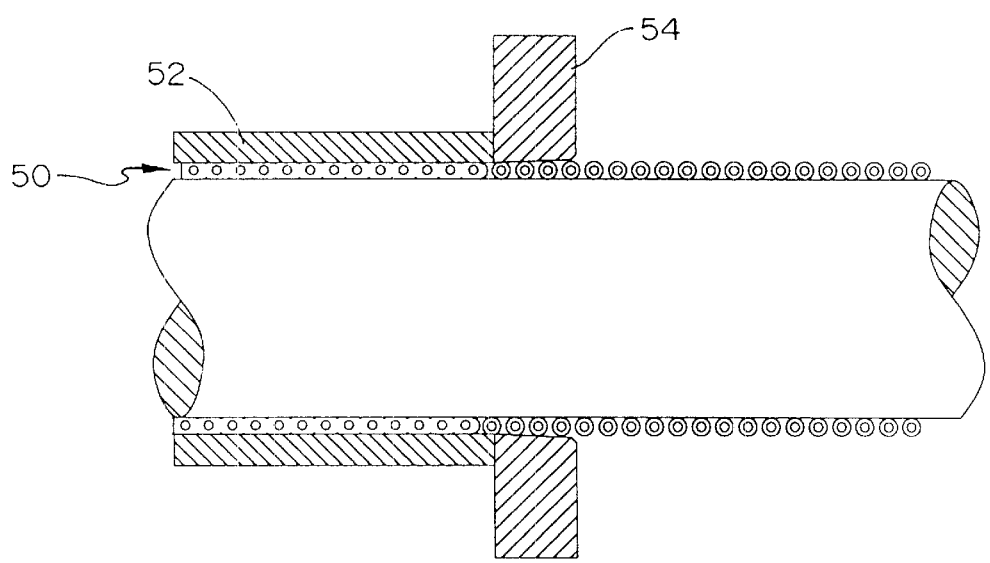
FIG. 4 is a partial cross-sectional side view of an extruder extruding an outer layer over an illustrative reinforcing member.

In another embodiment, the heat of the extrusion process of the outer layer is used to cause the thermoplastic polymer of the reinforcement layer to conform to the outer surface of the mandrel. Thus, a heated die may not be required. Such an embodiment is shown in FIG. 4. A reinforcement member 50 is provided over a mandrel, as described above with respect to FIG. 3. Then, an outer layer 52 is extruded over the reinforcement member 50 using extruder head 54. During the extrusion process, significant heat can be generated in the reinforcement member. Because the heat required to flow many thermoplastic polymers can be relatively low, it is contemplated that the heat from the extrusion process of the outer layer 52 may be sufficient to flow the thermoplastic polymer on the core wires of the reinforcing member 50.

In some embodiments, it may be desirable to use a non-thermoplastic polymer such as PTFE to coat the core wires of the strands of the reinforcing member. Such non-thermoplastic polymers do not readily flow when subject to heat. For PTFE, both heat and pressure may be required to change the shape of the polymer, but even then, the PTFE may not flow like a thermoplastic polymer.

Figure 5:
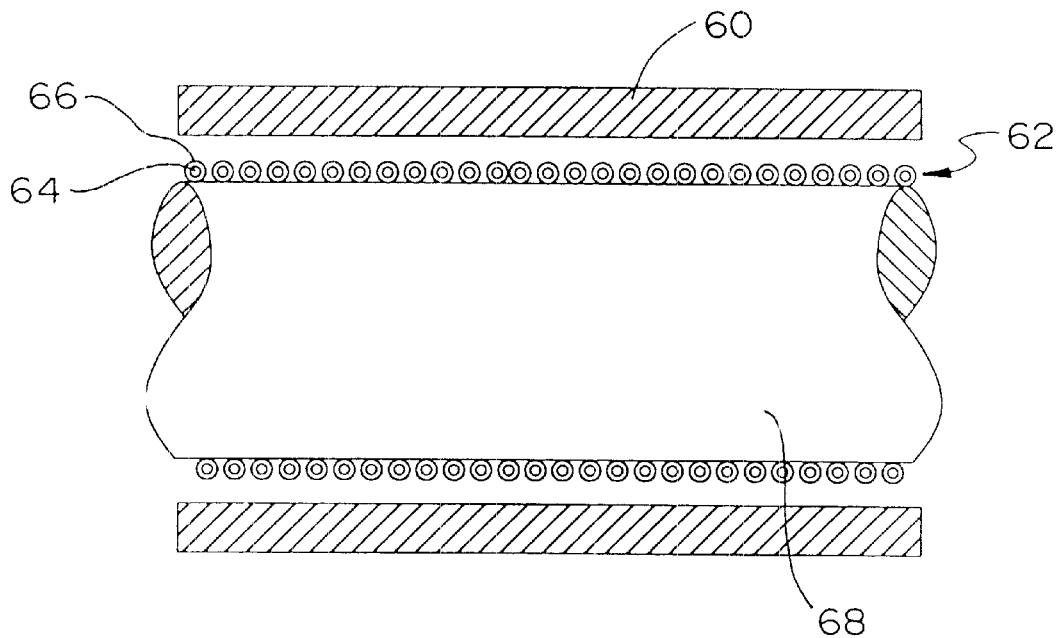
FIG. 5 is a partial cross-sectional side view of a reinforcing member enclosed in a heated die.

FIG. 5 is a partial cross-sectional side view of a heated die 60 applying heat and pressure to an illustrative reinforcing member 62. In this illustrative embodiment, each strand of the reinforcing member 62 has a core wire 64 formed from stainless steel or the like, which is coated with a non-thermoplastic polymer 66 such as PTFE. Like above, the reinforcing member 62 is preferably wound around a mandrel 68, as shown. Because of the relatively high heat and pressure required to change the shape of the PTFE polymer, the mandrel is preferably made from copper or silver coated copper. Other suitable mandrel materials can be used, for example, nylon coated stainless steel.

Figure 6:
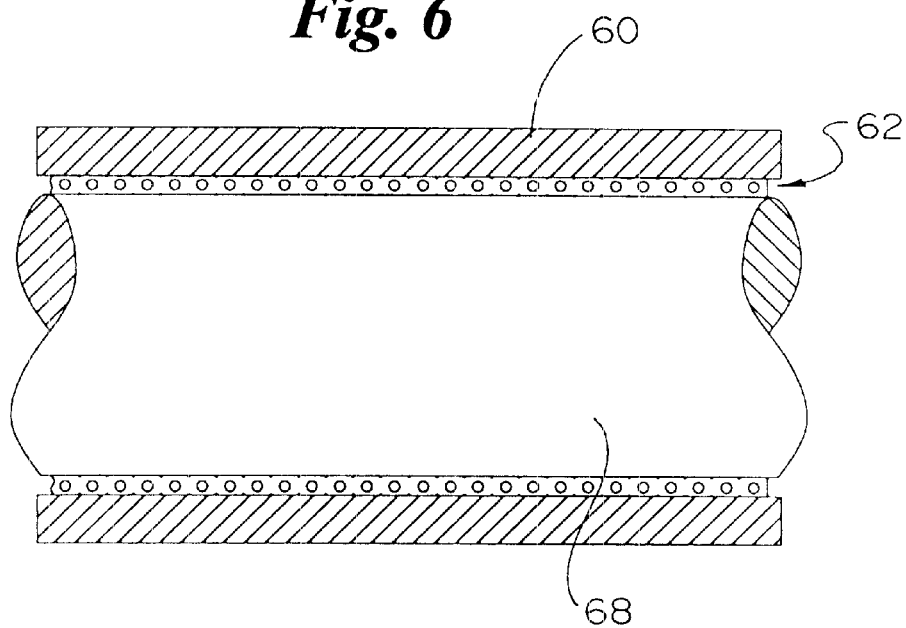
FIG. 6 is a partial cross-sectional side view of the reinforcing member of FIG. 5 after the heat and pressure are removed.

To shape the non-thermoplastic polymer that coats the core wires of the reinforcement member 62, a heated die 60 is provided around at least a portion of the outer surface of the reinforcing member 62. The heated die 60 applies both heat and pressure to the reinforcing member 66. The heat and pressure may cause the non-thermoplastic polymer 66 to conform to the shape of the outside surface of the mandrel 68 and the inside surface of the heated die 60. Once the non-thermoplastic polymer is properly formed, the result is a thin-walled reinforced non-thermoplastic tube around the mandrel 68, as shown in FIG. 6.

An outer layer (not shown) may then be extruded over the reinforcing member 62. To allow the outer layer to properly adhere to the reinforcing member 62, it may be desirable to etch the outer surface of the reinforcing member 62. Once etched, the outer layer may be extruded over the reinforcing member 62. Again, the outer layer is preferably formed from polyester, polyether block amide, nylon or some other thermoplastic polymer. Once the outer layer is extruded, the mandrel 68 is removed.

Although the present invention is described in terms of the preferred embodiment above, it should be noted that alterations and modifications of this invention will be possible without departing from the spirit and scope of this invention.

What is claimed is:

1. A method for forming a catheter shaft, the method comprising the steps of:
    winding one or more elongated strands around a mandrel, wherein selected strands have an inner core coated by a lubricious polymer, the wound elongated strands collectively forming an inner tubular reinforcing member;
    providing an outer tubular member over the inner tubular reinforcing member; and
    removing the mandrel.

2. A method according to claim 1, wherein the one or more elongated strands are wound to form a braid.

3. A method according to claim 2, wherein the braid is wound in a pattern that substantially prevents the extruded polymer of the outer tubular member from flowing through the inner tubular reinforcing member to the mandrel.

4. A method according to claim 1, wherein the providing step includes the step of extruding a polymer over the inner tubular reinforcing member to form the outer tubular member.

5. A method according to claim 1, wherein the one or more elongated strands are wound to form a coil.

6. A method according to claim 1, wherein the inner core of selected strands is stainless steel.

7. A method according to claim 1, wherein the lubricious polymer is polytetrafluoroethylene (PTFE).

8. A method according to claim 7, wherein the mandrel comprises a copper core coated with silver, and wherein the step of winding one or more elongated strands around a mandrel includes winding one or more elongated strands around the copper core mandrel coated with silver.

9. A method according to claim 7, further comprising the step of applying heat and pressure to the inner tubular reinforcing member before providing the outer tubular member.

10. A method according to claim 9, wherein the applied heat and pressure is sufficient to cause the polytetrafluoroethylene (PTFE) polymer that coats the inner core of selected strands to substantially conform to the shape of the mandrel.

11. A method according to claim 1, wherein the lubricious polymer is a perfluoroalkoxy polymer.

12. A method according to claim 11, wherein the mandrel is formed from an acetyl polymer, and wherein the step of winding one or more elongated strands around a mandrel includes winding one or more elongated strands around the acetyl polymer mandrel.

13. A method according to claim 11, further comprising the step of applying heat to the inner tubular reinforcing member before providing the outer tubular member.

14. A method according to claim 13, wherein the applied heat is sufficient to cause the perfluoroalkoxy polymer that coats the inner core of selected strands to flow and create a thin-walled liner adjacent the mandrel.

15. A method according to claim 13, wherein the heat is provided by a heated die.

16. A method according to claim 13, wherein the providing step includes the step of extruding a polymer over the inner tubular reinforcing member to form the outer tubular member.

17. A method according to claim 16, wherein the heat is applied by the extrusion of the outer tubular member.

18. A method according to claim 1, further comprising the step of etching an outer surface of the inner tubular reinforcing member before providing the outer layer.

19. A method for forming a catheter shaft, the method comprising the steps of:
    winding one or more elongated strands around a mandrel having a relatively smooth outer surface, wherein selected strands have an inner core coated by a lubricious polymer, the wound elongated strands collectively forming an inner tubular reinforcing member;
    applying heat to the inner tubular reinforcing member, wherein the heat is sufficient to cause the polymer that coats the inner core of selected strands to conform to the relatively smooth outer surface of the mandrel; and
    removing the mandrel.

20. A method according to claim 19, wherein the heat applying step further includes the step of applying inward pressure to the inner tubular reinforcing member toward the mandrel.

21. A method according to claim 19, further comprising the step of providing an outer tubular member over the inner tubular reinforcing member.

22. A method according to claim 21, further comprising the step of etching the outer surface of the inner tubular reinforcing member before providing the outer tubular member.

23. A method according to claim 21, wherein the outer tubular member is provided by extruding a polymer over the inner tubular reinforcing member.

24. A method according to claim 23, wherein the extruding step provides the heat for the heat applying step.

* * * * *